United States Patent [19]

Maki

[11] Patent Number: 5,002,511
[45] Date of Patent: Mar. 26, 1991

[54] STUFFED TOYS WITH HEAT RESPONSIVE INFRARED RADIATION

[75] Inventor: Tomohide Maki, Tokyo, Japan

[73] Assignee: Anmin Manufacturing Co., Ltd., Tokyo, Japan

[21] Appl. No.: 494,879

[22] Filed: Mar. 8, 1990

Related U.S. Application Data

[63] Continuation of Ser. No. 281,529, Dec. 9, 1988, abandoned.

[30] Foreign Application Priority Data

Dec. 18, 1987 [JP] Japan .................. 62-192470

[51] Int. Cl.$^5$ .................. A63H 33/00; A63H 3/00; A63H 3/02; C03C 4/10
[52] U.S. Cl. .................. 446/14; 446/74; 446/295; 446/369; 501/904; 5/421
[58] Field of Search .................. 446/14, 71, 72, 73, 446/74, 295, 296, 369, 385, 387; 501/904; 5/421

[56] References Cited

U.S. PATENT DOCUMENTS

| | | | |
|---|---|---|---|
| 1,274,328 | 7/1918 | Price | 446/369 X |
| 1,581,382 | 4/1926 | Buchtrup | 446/369 |
| 1,732,316 | 10/1929 | Scott | 446/369 X |
| 3,898,427 | 8/1975 | Levin et al. | 5/421 X |
| 4,204,110 | 5/1980 | Smit et al. | 446/72 X |
| 4,500,642 | 2/1985 | Reiji et al. | 501/904 X |
| 4,680,822 | 7/1987 | Fujino et al. | 5/421 |
| 4,694,829 | 9/1987 | Frye | 446/74 X |
| 4,714,445 | 12/1987 | Templeton | 446/369 X |
| 4,825,868 | 5/1989 | Susa et al. | 5/421 X |

FOREIGN PATENT DOCUMENTS

| | | | |
|---|---|---|---|
| 0232984 | 12/1984 | Japan | 501/904 |
| 033249 | 2/1985 | Japan | 501/904 |
| 6907225 | 11/1970 | Netherlands | 501/904 |
| 291886 | 1/1971 | U.S.S.R. | 501/904 |

*Primary Examiner*—Robert A. Hafer
*Assistant Examiner*—D. Neal Muir
*Attorney, Agent, or Firm*—Barnes, Kisselle, Raisch, Choate, Whittemore & Hulbert

[57] ABSTRACT

Stuffed toy used as ornaments, mascots and the like in which a filler is sealed into a bag-like body comprising a laminate wherein a pliable sheet having a far infrared radiation layer on one surface thereof is superposed to an inner side of a cover sheet with the far infrared radiation layer faced to the side of the cover sheet.

5 Claims, 1 Drawing Sheet

STUFFED TOYS WITH HEAT RESPONSIVE INFRARED RADIATION

Reference to Co-Pending Application

This is a continuation-in-part application of copending U.S. patent application, Ser. No. 07/281,529, filed on Dec. 9, 1988, now abandoned.

FIELD OF THE INVENTION

The present invention relates to a stuffed toy used as ornaments, mascots and the like.

RELATED ART STATEMENT

Many of stuffed toys used for toys, ornaments, mascots and the like are in the form of an animal, and are made by inserting a filler into a bag body made of a fur sheet. Accordingly, when one holds a stuffed toy (doll) in his (her) arms, fur on the surface touches a person's body such as hands to obtain a feeling such as softness thereof. However, since the stuffed doll is not higher in temperature than that of a person who holds the doll, the person will not receive heat from the stuffed doll.

Many pets such as cats are higher in temperature than that of a human being. Therefore, when a person holds a pet, heat is transferred from the pet to the person who holds the pet to receive a feeling of warmth. However, in the stuffed toy, such a feeling does not occur, and the feeling of warmth obtained when one holds the stuffed toy results only from the heat insulation effect of fur or the like of the surface of the stuffed toy.

In view of the foregoing, in order to generate heat from the interior of a stuffed toy to obtain a warmth higher than the human skin when one holds a stuffed toy, a so-called disposable pocket heater which utilizes chemical reaction of iron oxide has been inserted into the stuffed toy to generate heat from the interior of the stuffed toy. However, in the case where the disposable pocket heater or other heat generation member is inserted into the stuffed toy, the disposal pocket heater or the like has to be inserted whenever used, and in addition, if the other heat generation means is used, a danger of fire possibly occurs.

OBJECT AND SUMMARY OF THE INVENTION

It is an object of the present invention to provide a stuffed toy in which one may feel as if the stuffed toy itself has a temperature because of heat received from the interior of the stuffed toy.

A filler 9 is sealed into a body formed into a bag by a laminate 5 wherein a pliable sheet having a far infrared radiation layer on one surface thereof is laminated on an inner side of a cover sheet covering the outer surface of a stuffed toy with said far infrared radiation layer faced to the inside of the cover sheet.

In the stuffed toy according to the present invention, in the case where one holds or carries it in hands, when the far infrared radiation layer provided on the pliable sheet is heated by the temperature of a user to more or less than 36° C. in the region of temperature, the far infrared radiation is radiated from the far infrared radiation body heated by the temperature of person. This far infrared radiation permeates into 40 to 50 mm in the skin of a human being, and the absorbed radiation energy promotes the ionizing action of the interior of the body to activate cells to warm his very bones, exhibiting a state as if one may receive heat from a living pet.

DETAILED DESCRIPTION OF PREFERRED EMBODIMENTS

Figure 1:
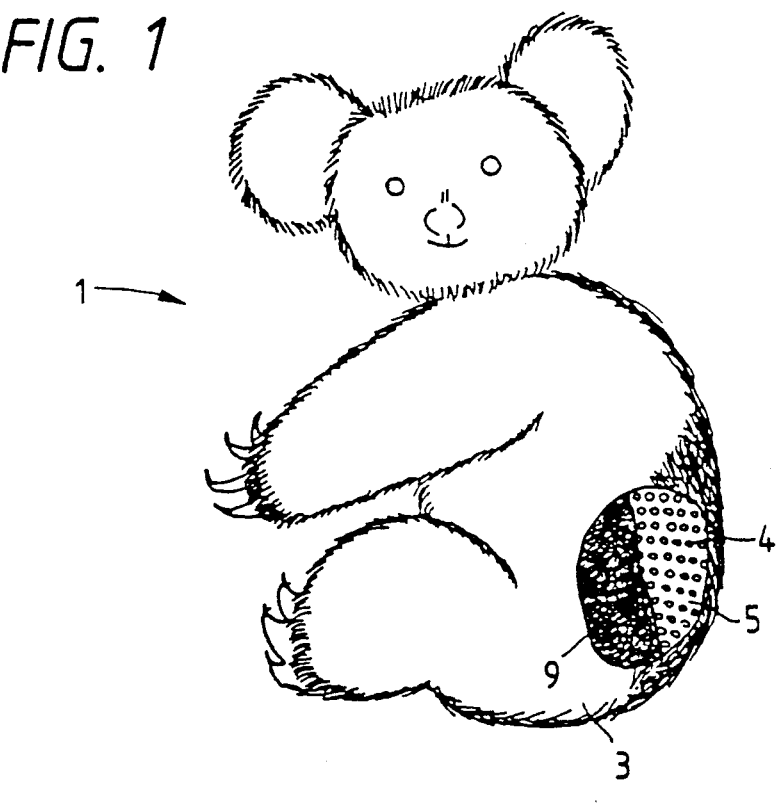
FIG. 1 is a perspective view showing a state in which a stuffed doll according to the present invention is partly cutaway.
Figure 2:
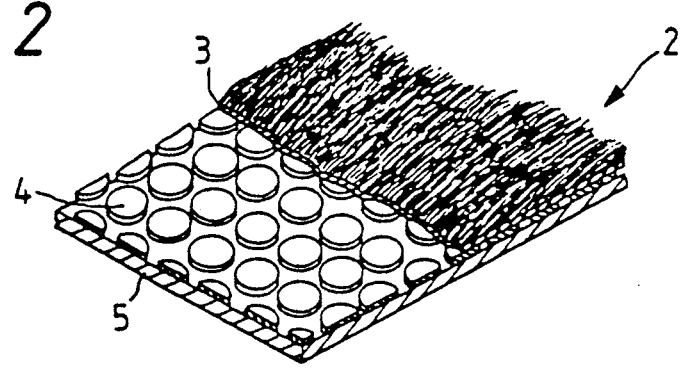
FIG. 2 is a perspective view of a laminate.
Figure 3:
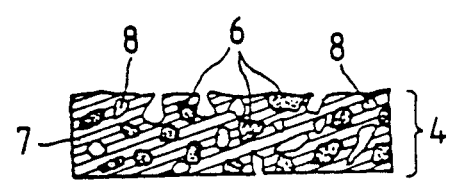
FIG. 3 is a sectional view of a far infrared radiation layer.

A stuffed toy 1 according to the present invention is made by a laminate 2 later introduced into an enclosure in the form of an animal, fish, a human being and other suitable configurations. The laminate 2 comprises a cover sheet 3 formed of a material of fur or the like exposed to the surface of the stuffed toy, and a pliable sheet 5 having a far infrared radiation layer 4 on one surface thereof. The cover sheet 3 is not always limited to the fur material depending on the character of stuffed toys to be made.

Materials for the pliable sheet 5 include woven fabrics, non-woven fabrics, synthetic resin films, metal foils or the like or a suitable laminate thereof. The far infrared radiation layer 4 includes a far infrared radiation body 6, which is formed of ceramics which are heated to radiate infrared rays of long wavelength, that is, a far infrared radiation. The aforesaid ceramics are obtained by mixing a conventional clay and a Kibushi clay (kaolinite), using the same as a base and adding a quartz rock pulverized material thereto, further adding oxide aluminum or oxide zirconium or oxide silicon and adding a suitable amount of water and a caking agent and blending them, calcining the same at a high temperature of more or less than 1,300° C., and pulverizing it into a fine particle material which can pass a 50 to 200 mesh screen, and, in a preferable range, a 100 mesh screen. The screen rating is the number of openings per linear inch. A degree of this pulverization is related to the radiation of the far infrared rays later described. There are several factors which must be considered to optimize the size of the particles. Basic texts on the subject of radiation teach that the quantity of radiant heat transferred from a radiating body depends, in part, on the surface area of the radiating body and a shape factor. Both factors were considered, along with the need to satisfy the feeling of the final product when held by a person. These criteria were all considered and it was found that a particle size in the ranges set forth above were optimal. For a discussion of radiant heat transfer, see Chapter 10 of the *Chemical Engineer's Handbook*, 4th Edition, by John H. Perry.

The far infrared radiation body 6 radiates an electromagnetic wave whose wavelength leak in the region of body temperature is 7 to 14μ, and radiates far infrared rays of the aforesaid wavelength in coincidence with the infrared absorption wavelength body of a human body by the temperature of 36° C. or so which is nearly equal to the body temperature.

The far infrared radiation bodies 6 are coated in a suitable thickness on both or one surface of the pliable sheet 2 adding a binder 7 formed, for example, of an acrylic resin to form the far infrared radiation layer 4. A foaming agent may be added to the binder as needed.

It was found that oxides selected from aluminum oxide, zirconium oxide, silicon oxide, lithium oxide, iron oxide, calcium oxide and magnesium oxide can be used in the process.

The preferred oxide composition comprises 70% to 80% silicon oxide, 10% to 20% aluminum oxide, up to 10% iron oxide, up to 5% magnesium oxide, and up to 5% calcium oxide.

In addition, it is preferable that the oxides comprise oxides of the following formulas: silicon oxide comprising $SiO_2$, aluminum oxide comprising $Al_2O_3$, iron oxide comprising $Fe_2O_3$, lithium oxide comprising $Li_2O$, magnesium oxide comprising MgO and calcium oxide comprising CaO.

The foaming agent mixed into the far infrared radiation layer 4 foams at the time of heat treatment after coating to generate continuous bubbles 8 in the layer 4. The pliable sheet 5 having the far infrared radiation layer 4 on the surface thereof and the cover sheet 3 are superposed so that the far infrared radiation layer 4 is adjacent the cover sheet 3 to form the laminate 2. It is noted that the aforesaid superposition may be a mere superposition or any integration means such as adhesive or quilt may be used therebetween.

The stuffed toy 1 is sewn into a bag-like configuration by the laminate 2, a filler 9 is sealed therein, and an opening provided in a suitable location is closed.

In the case where this stuffed toy 1 is carried by hands or held, the heat from the body is absorbed into the far infrared radiation body 6 of the far infrared radiation layer 4, whereby the far infrared radiation body 6 assumes a temperature of more or less than 36° C. which is nearly equal to that of the body temperature. At that temperature, the far infrared radiation body 6 radiates an electromagnetic wave whose wavelength peak is 7 to 14$\mu$ in coincidence with the infrared ray absorption wavelength band of a human being. Thus far infrared rays are well absorbed into the human body and permeates into 40 to 50 mm under the skin, and the absorbed radiation energy promotes the ionizing action within the body to activate cells and warm the very bones of the body, providing a feeling of being warmed by the stuffed toy as if the stuffed toy is alive.

In the stuffed toy according to the present invention, a filler is sealed into a bag-like body comprising a laminate wherein a pliable sheet having a far infrared radiation layer on the surface thereof is superposed to an inner side of a cover sheet with said far infrared radiation layer faced to the cover sheet. Therefore, one receives an irradiation of the far infrared rays from the far infrared radiation body of the stuffed toy warmed by carrying or holding the stuffed toy in arms, whereby the person who holds the stuffed toy is warmed from the interior of the body by the far infrared rays not only to obtain a warm feeling as if the stuffed toy is alive but the present stuffed toy can be used by a child without any danger in contrast to those toys in which a so-called pocket heater, which utilizes electric heat or chemical reaction, is inserted into the stuffed toy.

What is claimed is:

1. A stuffed toy of predetermined shape comprising:
    a cover sheet of soft material enclosing said toy,
    a soft filler material in the interior of said toy,
    a pliable laminate layer sheet inside and directly adjacent said cover sheet comprising an infrared radiation layer on one surface thereto facing the inside surface of said cover sheet,
    said infrared layer comprising calcined and pulverized ceramic particles comprising:
    (a) a mixture of clay and Kaolinite as a base,
    (b) a quantity of pulverized quartz rock,
    (c) an oxide selected from aluminum oxide, zirconium oxide, silicon oxide, lithium oxide, iron oxide, calcium oxide and magnesium oxide, and
    (d) a caking agent,
    said particles having a preferred mesh size of 50 to 200, and
    whereby said radiation layer, when warmed to approximately 36° C. by human body heat, radiated electromagnetic waves with a peak wavelength of from 7 to 14 microns.

2. The pulverized ceramic particles of claim 1 comprising said oxide comprising 70% to 80% silicon oxide, 10% to 20% aluminum oxide, up to 10% iron oxide, up to 5% magnesium oxide, and up to 5% calcium oxide.

3. The oxide of claim 2 wherein said silicon oxide comprises $SiO_2$, said aluminum oxide comprises $Al_2O_3$, said iron oxide comprises $Fe_2O_3$, said lithium oxide comprises $Li_2O$, said magnesium oxide comprises MgO and said calcium oxide comprises CaO.

4. A stuffed toy as defined in claim 1 in which said particle mesh size is in the range of 100.

5. A stuffed toy as defined in claim 1 in which a foamed agent is mixed with said infrared layer to generate bubbles in said layer.

* * * * *